US009271636B2

(12) United States Patent
Teder et al.

(10) Patent No.: US 9,271,636 B2
(45) Date of Patent: Mar. 1, 2016

(54) SURGICAL ILLUMINATOR

(71) Applicant: Enova Illumination, LLC, St. Paul, MN (US)

(72) Inventors: Rein Teder, Bloomington, MN (US); Roger William Heegaard, St. Paul, MN (US)

(73) Assignee: Enova Illumination, LLC, St. Paul, MN (US)

( * ) Notice: Subject to any disclaimer, the term of this patent is extended or adjusted under 35 U.S.C. 154(b) by 235 days.

(21) Appl. No.: 14/021,113

(22) Filed: Sep. 9, 2013

(65) Prior Publication Data

US 2015/0073227 A1    Mar. 12, 2015

(51) Int. Cl.
*A61B 1/06* (2006.01)
*A61B 19/00* (2006.01)

(52) U.S. Cl.
CPC ............. *A61B 1/06* (2013.01); *A61B 1/0684* (2013.01); *A61B 1/0692* (2013.01); *A61B 2019/262* (2013.01); *A61B 2019/521* (2013.01)

(58) Field of Classification Search
CPC ...... A61B 1/06; A61B 1/0684; A61B 1/0692; A61B 2019/521
USPC .......... 600/246, 245, 199, 200; 362/105, 268, 362/804, 308, 309, 202, 171, 178, 294, 373, 362/800, 103, 418, 572, 187, 190, 191; 359/649, 651, 799, 800
See application file for complete search history.

(56) References Cited

U.S. PATENT DOCUMENTS

| | | | |
|---|---|---|---|
| 3,285,242 A * | 11/1966 | Wallace | 600/249 |
| 5,742,392 A | 4/1998 | Anderson et al. | |
| 5,774,271 A | 6/1998 | Lagerway et al. | |
| 7,490,949 B2 | 2/2009 | Medinis | |
| 7,645,050 B2 | 1/2010 | Wilt et al. | |
| 7,690,806 B2 | 4/2010 | Feinbloom et al. | |
| 7,758,204 B2 | 7/2010 | Klipstein et al. | |
| 7,883,233 B2 | 2/2011 | Feinbloom et al. | |
| 2006/0039160 A1 | 2/2006 | Cassarly et al. | |
| 2011/0122598 A1 | 5/2011 | Chang | |
| 2014/0334159 A1 * | 11/2014 | Ferguson | 362/311.02 |

* cited by examiner

*Primary Examiner* — Jerry Cumberledge
*Assistant Examiner* — David C Comstock
(74) *Attorney, Agent, or Firm* — Mitchell A. Rossman; Terra Nova Patent Law, PLLC

(57) ABSTRACT

The present invention provides a surgical illuminator. The surgical illuminator includes: a cylindrical lens barrel, a base, a printed circuit board, a light emitting diode, an aspheric lens, and a double-convex lens. Methods of using the surgical illuminator are also provided.

24 Claims, 3 Drawing Sheets

SURGICAL ILLUMINATOR

BACKGROUND OF THE INVENTION

High quality illumination is essential in medical applications, particularly in a surgical environment. Uneven illumination over the field of view may cause a surgeon to perceive problems that do not actually exist in the patient. Further, illumination anomalies and artifacts clutter and may distort the doctor's field of view, and may thus cause the doctor to miss details critical to the doctor's performance. Stray light beyond the desired illumination field distracts the doctor. Also, it is highly desirable to be able to adjust the spot of the illumination, so that only the area under consideration is seen by the doctor. Thus, medical professionals have long sought the best possible illumination in pursuit of the best possible outcomes.

With the advent of high power, light emitting diodes (LEDs), medical illuminators have used these devices as a light source. The light emitting diode based systems have the difficulty that the light source, the light emitting diode die, is typically square. Moreover, the top of the light emitting diode die invariably has some form of connecting wires, metallization or other structures to conduct electricity into the silicon. These conductors are generally not visible in typical light emitting diodes deployments where light emitting diodes illuminate a broad field. In a surgical illuminator, however, that images the light emitting diode onto the viewing surface, the light emitting diode die conductors are clearly visible and they degrade the light quality. The light emitting diode based surgical illuminators typically image the light emitting diode die onto the viewing plane to achieve a small spot size, and thus the spot is either a square or show at least the remnants of that square. Most doctors that use illuminators have been trained using fiber-optic illumination systems that emit circular illuminated spots. They are used to seeing bright circles, and prefer them.

While light emitting diodes are generally more efficient than incandescent sources, they still generate considerable heat. Inefficient dissipation of the heat can cause failure or degradation of the light emitting diode. Further, if the case of the illuminator gets hot, it can become difficult to touch. This can cause operator discomfort, as well as making it difficult to adjust or aim the beam by touching and moving the case.

What is needed is a surgical illuminator that avoids the deficiencies of the prior art.

SUMMARY OF THE INVENTION

The present invention provides a surgical illuminator that produces a clear, bright and adjustable spot without illumination anomalies and artifacts. The surgical illuminator is specifically designed for narrow depth of focus about the light emitting die and delivers a round spot on the viewing plane, with sharp edges. The optical efficiency of the surgical illuminator is high, and thus the spot is bright. The spot is free from the uneven illumination that has limited the acceptance of many light emitting diode based surgical illuminators. Further, the surgical illuminator is designed for thermal efficiency, yielding good light emitting diode life and no difficulties in touching the product during operation. Taken as a whole, the surgical illuminator produces performance that is on par with the fiber-optic illumination systems that surgeons are used to.

The enhanced performance of the surgical illuminator permits advancements in medical care. Surgeons have long found the fiber-optic tether of conventional systems to be uncomfortable, fatiguing, and restrictive. Thus, the surgical illuminator helps facilitate long surgeries. Further, many scenarios could benefit from surgical-suite quality lighting in a mobile situation. These scenarios include developing nations, emergency response, and field-military deployments.

The present invention provides a surgical illuminator with a round, adjustable beam, with high brightness and a clear field of view. The surgical illuminator produces an illumination spot this is free from illumination artifacts present on the light emitting diode die, which is the source of the illumination. Further, the surgical illuminator provides good cooling for the light emitting diode, yet provides that the beam adjustment mechanism not require that the user touch a hot surface.

The present invention provides a surgical illuminator. The surgical illuminator includes: a cylindrical lens barrel having a proximal end, a distal end, a first surface, and a second surface, wherein the proximal end of the second surface of the cylindrical lens barrel is connected to a cylindrical knurled ring with threads, wherein the proximal end of the first surface of the cylindrical lens barrel includes one or more holes, wherein the distal end of the second surface of the cylindrical lens barrel includes one or more fins; a base having a first surface, second surface, and a third surface including one or more helical grooves, wherein the base is mounted within the first surface of the cylindrical lens barrel with the one or more helical grooves and held in place with one or more cam followers protruding from the one or more holes into the one or more helical grooves, wherein the one or more helical groves each independently span about 270 degrees; a printed circuit board having a first surface and a second surface, wherein the first surface of the printed circuit board is connected to the second surface of the base; a light emitting diode coupled to the second surface of the printed circuit board; an aspheric lens having a planar surface and a convex surface, wherein the aspheric lens is mounted axially inside the cylindrical lens barrel so that the planar surface is facing the light emitting diode; and a double-convex lens having a first surface and a second surface, wherein the double-convex lens is mounted axially inside the cylindrical lens barrel so the convex surface of the aspheric lens is facing the first surface of the double-convex lens.

In one embodiment, the outside surface of the double-convex lens is adjacent to an O-ring adjacent to a circular constriction on the first surface of the cylindrical lens barrel.

In one embodiment, the first surface of the base is connected to a headlamp mounting bracket. In one embodiment, the light emitting diode includes a light emitting die contained within a light emitting diode body having a spherical optical surface having about a 1 mm radius of curvature. In one embodiment, the light emitting diode includes a square light emitting die contained within a light emitting diode body having a spherical optical surface having about a 1 mm radius of curvature. In one embodiment, the light emitting diode includes a circular light emitting die contained within a light emitting diode body having a spherical optical surface having about a 1 mm radius of curvature. In one embodiment, the light emitting diode includes an elliptical light emitting die contained within a light emitting diode body having a spherical optical surface having about a 1 mm radius of curvature.

In one embodiment, the exterior surface of the light emitting die includes one or more surface metallization artifacts.

In one embodiment, the light emitting diode features about an 80 degree radiation pattern, and maximum forward current of about 800 mA. In one embodiment, the light emitting diode operates with a current of about 100 mA to about 800 mA. In one embodiment, the surgical illuminator further includes a power source operatively connected to the printed circuit board.

In one embodiment, the power source includes an on/off switch. In one embodiment, the distance (Do) between the second surface of the printed circuit board and the planar surface of the aspheric lens is from about 8 mm. In one embodiment, the aspheric lens has a diameter of about 25 mm and a focal length of about 17.5 mm.

In one embodiment, the aspheric lens includes a polymeric material. In one embodiment, the double convex lens has a diameter of about 25 mm and a focal length of about 75 mm. In one embodiment, the double convex lens includes a glass. In one embodiment, the surgical illuminator further includes a spacer between the convex surface of the aspheric lens and the first surface of the double-convex lens. In one embodiment, the surgical illuminator further includes one or more filters detachably and axially mounted to the distal end of the cylindrical lens barrel. In one embodiment, the one or more filters detachably and axially mounted to the distal end of the cylindrical lens barrel with one or more threads. In one embodiment, the one or more filters detachably and axially mounted to the distal end of the cylindrical lens barrel with one or more internal threads.

In one embodiment, the surgical illuminator further includes a headlamp band. In one embodiment, the O-ring has a square cross-section. In one embodiment, the slot in third surface of the base contains an O-ring. In one embodiment, the O-ring has a round cross-section.

The present invention provides a surgical illuminator. The surgical illuminator includes: a cylindrical lens barrel having a proximal end, a distal end, a first surface, and a second surface, wherein the proximal end of the second surface of the cylindrical lens barrel is connected to a cylindrical knurled ring with threads, wherein the proximal end of the first surface of the cylindrical lens barrel includes one or more holes, wherein the distal end of the second surface of the cylindrical lens barrel includes one or more fins; a base having a first surface, second surface, and a third surface including one or more helical grooves, wherein the base is mounted within the first surface of the cylindrical lens barrel with the one or more helical grooves and held in place with one or more cam followers protruding from the one or more holes into the one or more helical grooves, wherein the first surface of the base is connected to a headlamp mounting bracket, wherein the one or more helical groves each independently span about 270 degrees; a printed circuit board having a first surface and a second surface, wherein the first surface of the printed circuit board is connected to the second surface of the base; a light emitting diode coupled to the second surface of the printed circuit board, wherein the light emitting diode includes a light emitting die contained within a light emitting diode body having a spherical optical surface having about a 1 mm radius of curvature, wherein an exterior surface of the light emitting die includes one or more surface metallization artifacts, an aspheric lens having a planar surface and a convex surface, wherein the aspheric lens is mounted axially inside the cylindrical lens barrel so that the planar surface is facing the light emitting diode, wherein a distance (Do) between the second surface of the printed circuit board and the planar surface of the aspheric lens is from about 8 mm, wherein the aspheric lens has a diameter of about 25 mm and a focal length of about 17.5 mm; and a double-convex lens having a first surface and a second surface, wherein the double-convex lens is mounted axially inside the cylindrical lens barrel so the convex surface of the aspheric lens is facing the first surface of the double-convex lens, wherein the double convex lens has a diameter of about 25 mm and a focal length of about 75 mm, wherein a distance between the convex surface of the aspheric lens and the first surface of the double-convex lens is set with a spacer.

In one embodiment, the light emitting diode features about an 80 degree radiation pattern, and maximum forward current of about 800 mA. In one embodiment, the light emitting diode operates with a current of about 100 mA to about 800 mA. In one embodiment, the surgical illuminator further includes a power source operatively connected to the printed circuit board. In one embodiment, the power source includes an on/off switch. In one embodiment, the aspheric lens includes a polymeric material. In one embodiment, the double convex lens includes a glass. In one embodiment, the surgical illuminator further includes one or more filters detachably and axially mounted to the distal end of the cylindrical lens barrel. In one embodiment, the surgical illuminator further includes a headlamp band connected to the headlamp mounting bracket.

The present invention provides a surgical illuminator. The surgical illuminator includes: a cylindrical lens barrel having a proximal end, a distal end, a first surface, and a second surface, wherein the proximal end of the second surface of the cylindrical lens barrel is connected to a cylindrical knurled ring with threads, wherein the proximal end of the first surface of the cylindrical lens barrel includes one or more holes, wherein the distal end of the second surface of the cylindrical lens barrel includes one or more fins; a base having a first surface, second surface, and a third surface including one or more helical grooves, wherein the base is mounted within the first surface of the cylindrical lens barrel with the one or more helical grooves and held in place with one or more cam followers protruding from the one or more holes into the one or more helical grooves, wherein the first surface of the base is connected to a headlamp mounting bracket, wherein the one or more helical groves each independently span about 270 degrees; a printed circuit board having a first surface and a second surface, wherein the first surface of the printed circuit board is connected to the second surface of the base; a light emitting diode coupled to the second surface of the printed circuit board, wherein the light emitting diode includes a light emitting die contained within a light emitting diode body having a spherical optical surface having about a 1 mm radius of curvature, wherein an exterior surface of the light emitting die includes one or more surface metallization artifacts, wherein the light emitting diode features about an 80 degree radiation pattern, and maximum forward current of about 800 mA, wherein the light emitting diode operates with a current of about 100 mA to about 800 mA; a power source operatively connected to the printed circuit board, wherein the power source includes an on/off switch; an aspheric lens having a planar surface and a convex surface, wherein the aspheric lens is mounted axially inside the cylindrical lens barrel so that the planar surface is facing the light emitting diode, wherein a distance (Do) between the second surface of the printed circuit board and the planar surface of the aspheric lens is from about 8 mm, wherein the aspheric lens has a diameter of about 25 mm and a focal length of about 17.5 mm; a double-convex lens having a first surface and a second surface, wherein the double-convex lens is mounted axially inside the cylindrical lens barrel so the convex surface of the aspheric lens is facing the first surface of the double-convex lens, wherein the double convex lens has a diameter of about 25 mm and a focal length of about 75 mm, wherein a distance between the convex surface of the aspheric lens and the first surface of the double-convex lens is set with a spacer; one or more filters detachably and axially mounted to the distal end of the cylindrical lens barrel; a headlamp band connected to the headlamp mounting bracket.

The present invention provides a method of using a surgical illuminator. The method includes: providing a surgical illuminator including: a cylindrical lens barrel having a proximal end, a distal end, a first surface, and a second surface, wherein the proximal end of the second surface of the cylindrical lens barrel is connected to a cylindrical knurled ring with threads, wherein the proximal end of the first surface of the cylindrical lens barrel includes one or more holes, wherein the distal end of the second surface of the cylindrical lens barrel includes one or more fins; a base having a first surface, second surface, and a third surface including one or more helical grooves, wherein the base is mounted within the first surface of the cylindrical lens barrel with the one or more helical grooves and held in place with one or more cam followers protruding from the one or more holes into the one or more helical grooves, wherein the one or more helical groves each independently span about 270 degrees; a printed circuit board having a first surface and a second surface, wherein the first surface of the printed circuit board is connected to the second surface of the base; a light emitting diode coupled to the second surface of the printed circuit board; an aspheric lens having a planar surface and a convex surface, wherein the aspheric lens is mounted axially inside the cylindrical lens barrel so that the planar surface is facing the light emitting diode; and a double-convex lens having a first surface and a second surface, wherein the double-convex lens is mounted axially inside the cylindrical lens barrel so the convex surface of the aspheric lens is facing the first surface of the double-convex lens; attaching the surgical illuminator to the head of a surgeon; turning on the surgical illuminator; and illuminating an object.

The present invention provides a method of using a surgical illuminator. The method includes: providing a surgical illuminator including: a cylindrical lens barrel having a proximal end, a distal end, a first surface, and a second surface, wherein the proximal end of the second surface of the cylindrical lens barrel is connected to a cylindrical knurled ring with threads, wherein the proximal end of the first surface of the cylindrical lens barrel includes one or more holes, wherein the distal end of the second surface of the cylindrical lens barrel includes one or more fins; a base having a first surface, second surface, and a third surface including one or more helical grooves, wherein the base is mounted within the first surface of the cylindrical lens barrel with the one or more helical grooves and held in place with one or more cam followers protruding from the one or more holes into the one or more helical grooves, wherein the first surface of the base is connected to a headlamp mounting bracket, wherein the one or more helical groves each independently span about 270 degrees, wherein the third surface of the base includes a slot containing an O-ring; a printed circuit board having a first surface and a second surface, wherein the first surface of the printed circuit board is connected to the second surface of the base; a light emitting diode coupled to the second surface of the printed circuit board, wherein the light emitting diode includes a light emitting die contained within a light emitting diode body having a spherical optical surface having about a 1 mm radius of curvature, wherein an exterior surface of the light emitting die includes one or more surface metallization artifacts, an aspheric lens having a planar surface and a convex surface, wherein the aspheric lens is mounted axially inside the cylindrical lens barrel so that the planar surface is facing the light emitting diode, wherein a distance (Do) between the second surface of the printed circuit board and the planar surface of the aspheric lens is from about 8 mm, wherein the aspheric lens has a diameter of about 25 mm and a focal length of about 17.5 mm; and a double-convex lens having a first surface and a second surface, wherein the double-convex lens is mounted axially inside the cylindrical lens barrel so the convex surface of the aspheric lens is facing the first surface of the double-convex lens, wherein the double convex lens has a diameter of about 25 mm and a focal length of about 75 mm, wherein a distance between the convex surface of the aspheric lens and the first surface of the double-convex lens is set with a spacer; attaching the surgical illuminator to the head of a surgeon; turning on the surgical illuminator; and illuminating an object.

The present invention provides a method of using a surgical illuminator. The method includes: providing a surgical illuminator including: a cylindrical lens barrel having a proximal end, a distal end, a first surface, and a second surface, wherein the proximal end of the second surface of the cylindrical lens barrel is connected to a cylindrical knurled ring with threads, wherein the proximal end of the first surface of the cylindrical lens barrel includes one or more holes, wherein the distal end of the second surface of the cylindrical lens barrel includes one or more fins; a base having a first surface, second surface, and a third surface including one or more helical grooves, wherein the base is mounted within the first surface of the cylindrical lens barrel with the one or more helical grooves and held in place with one or more cam followers protruding from the one or more holes into the one or more helical grooves, wherein the first surface of the base is connected to a headlamp mounting bracket, wherein the one or more helical groves each independently span about 270 degrees; a printed circuit board having a first surface and a second surface, wherein the first surface of the printed circuit board is connected to the second surface of the base; a light emitting diode coupled to the second surface of the printed circuit board, wherein the light emitting diode includes a light emitting die contained within a light emitting diode body having a spherical optical surface having about a 1 mm radius of curvature, wherein an exterior surface of the light emitting die includes one or more surface metallization artifacts, wherein the light emitting diode features about an 80 degree radiation pattern, and maximum forward current of about 800 mA, wherein the light emitting diode operates with a current of about 100 mA to about 800 mA; a power source operatively connected to the printed circuit board, wherein the power source includes an on/off switch; an aspheric lens having a planar surface and a convex surface, wherein the aspheric lens is mounted axially inside the cylindrical lens barrel so that the planar surface is facing the light emitting diode, wherein a distance (Do) between the second surface of the printed circuit board and the planar surface of the aspheric lens is from about 8 mm, wherein the aspheric lens has a diameter of about 25 mm and a focal length of about 17.5 mm; a double-convex lens having a first surface and a second surface, wherein the double-convex lens is mounted axially inside the cylindrical lens barrel so the convex surface of the aspheric lens is facing the first surface of the double-convex lens, wherein the double convex lens has a diameter of about 25 mm and a focal length of about 75 mm, wherein a distance between the convex surface of the aspheric lens and the first surface of the double-convex lens is set with a spacer; one or more filters detachably and axially mounted to the distal end of the cylindrical lens barrel; a headlamp band connected to the headlamp mounting bracket; one or more filters detachably and axially mounted to the distal end of the cylindrical lens barrel; and a headlamp band connected to the headlamp mounting bracket; attaching the surgical illuminator to the head of a surgeon; turning on the surgical illuminator; and illuminating an object.

BRIEF DESCRIPTION OF THE DRAWINGS

Embodiments of the invention may be best understood by referring to the following description and accompanying drawings, which illustrate such embodiments. In the drawings.

Figure 1:
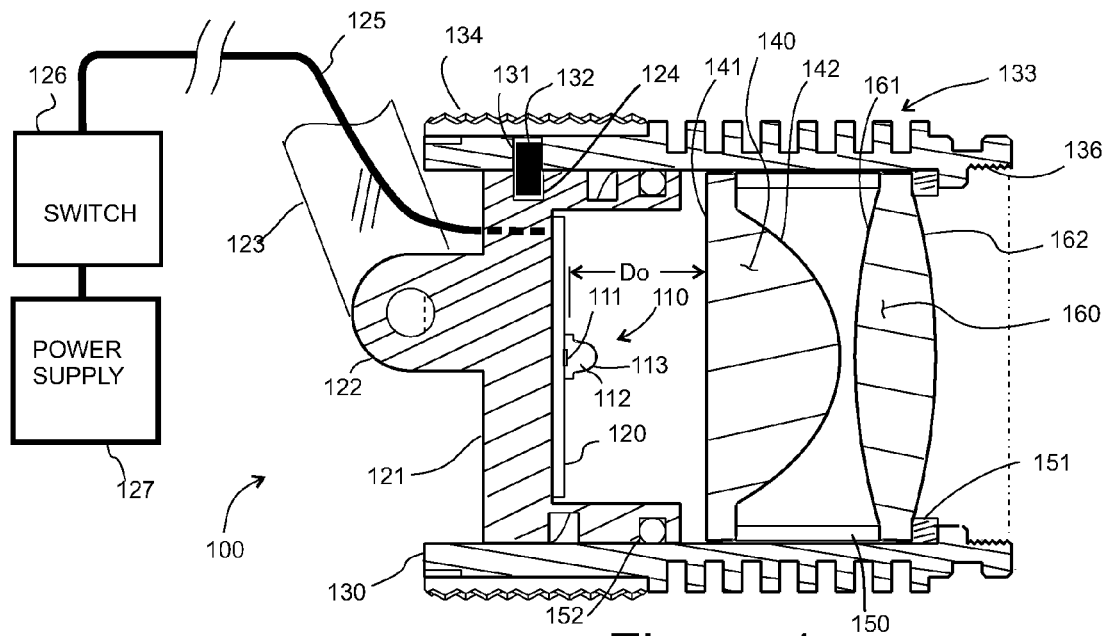
FIG. 1 is a side-view cross-sectional drawing illustrating an exemplary surgical illuminator.

The drawings are not necessarily to scale. Like numbers used in the figures refer to like components, steps, and the like. However, it will be understood that the use of a number to refer to a component in a given figure is not intended to limit the component in another figure labeled with the same number.

DETAILED DESCRIPTION OF THE INVENTION

The present invention provides a surgical illuminator. The surgical illuminator includes: a cylindrical lens barrel having a proximal end, a distal end, a first surface, and a second surface, wherein the proximal end of the second surface of the cylindrical lens barrel is connected to a cylindrical knurled ring with threads, wherein the proximal end of the first surface of the cylindrical lens barrel includes one or more holes, wherein the distal end of the second surface of the cylindrical lens barrel includes one or more fins; a base having a first surface, second surface, and a third surface including one or more helical grooves, wherein the base is mounted within the first surface of the cylindrical lens barrel with the one or more helical grooves and held in place with one or more cam followers protruding from the one or more holes into the one or more helical grooves, wherein the one or more helical groves each independently span about 270 degrees; a printed circuit board having a first surface and a second surface, wherein the first surface of the printed circuit board is connected to the second surface of the base; a light emitting diode coupled to the second surface of the printed circuit board; an aspheric lens having a planar surface and a convex surface, wherein the aspheric lens is mounted axially inside the cylindrical lens barrel so that the planar surface is facing the light emitting diode; and a double-convex lens having a first surface and a second surface, wherein the double-convex lens is mounted axially inside the cylindrical lens barrel so the convex surface of the aspheric lens is facing the first surface of the double-convex lens. In one embodiment, the outside surface of the double-convex lens is adjacent to an O-ring adjacent to a circular constriction on the first surface of the cylindrical lens barrel.

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, and logical changes may be made without departing from the scope of the present invention. The following detailed description is, therefore, not to be taken in a limiting sense, and the scope of the present invention is defined by the appended claims and their equivalents.

Before the present invention is described in such detail, however, it is to be understood that this invention is not limited to particular variations set forth and may, of course, vary. Various changes may be made to the invention described and equivalents may be substituted without departing from the true spirit and scope of the invention. In addition, many modifications may be made to adapt a particular situation, material, composition of matter, process, process act(s) or step(s), to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

The referenced items are provided solely for their disclosure prior to the filing date of the present application. Nothing herein is to be construed as an admission that the present invention is not entitled to antedate such material by virtue of prior invention.

Unless otherwise indicated, the words and phrases presented in this document have their ordinary meanings to one of skill in the art. Such ordinary meanings can be obtained by reference to their use in the art and by reference to general and scientific dictionaries, for example, *Webster's Third New International Dictionary*, Merriam-Webster Inc., Springfield, Mass., 1993 and *The American Heritage Dictionary of the English Language*, Houghton Mifflin, Boston Mass., 1981.

References in the specification to "one embodiment" indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The following explanations of certain terms are meant to be illustrative rather than exhaustive. These terms have their ordinary meanings given by usage in the art and in addition include the following explanations.

As used herein, the term "about" refers to a variation of 10 percent of the value specified; for example about 50 percent carries a variation from 45 to 55 percent.

As used herein, the term "and/or" refers to any one of the items, any combination of the items, or all of the items with which this term is associated.

As used herein, the singular forms "a," "an," and "the" include plural reference unless the context clearly dictates otherwise. It is further noted that the claims may be drafted to exclude any optional element. As such, this statement is intended to serve as antecedent basis for use of such exclusive terminology as "solely," "only," and the like in connection with the recitation of claim elements, or use of a "negative" limitation.

As used herein, the term "coupled" means the joining of two members directly or indirectly to one another. Such joining may be stationary in nature or movable in nature and/or such joining may allow for the flow of fluids, electricity, electrical signals, or other types of signals or communication between two members. Such joining may be achieved with the two members or the two members and any additional intermediate members being integrally formed as a single unitary body with one another or with the two members or the two members and any additional intermediate members being attached to one another. Such joining may be permanent in nature or alternatively may be removable or releasable in nature.

As used herein, the term "Di" refers to the distance from the double convex lens to the image focal point.

As used herein, the term "Do" refers to the distance from the light emitting diode to the aspheric lens.

As used herein, the term "electromagnetic radiation" refers to a series of waves that are propagated by simultaneous periodic variations of electric and magnetic field intensity and that include radio waves, infrared, visible light, ultraviolet, X rays, and gamma rays.

As used herein, the terms "include," "for example," "such as," and the like are used illustratively and are not intended to limit the present invention.

As used herein, the term "light" refers to an electromagnetic radiation in the wavelength range including infrared, visible, ultraviolet, and X rays.

As used herein, the phrase "light emitting diode" or "LED" refers to a diode that emits light, whether visible, ultraviolet, or infrared, and whether coherent or incoherent. The term as used herein includes incoherent epoxy-encased semiconductor devices marketed as used herein, "LEDs," whether of the conventional or super-radiant variety. The term as used herein also includes semiconductor laser diodes.

As used herein, the term "optical" refers to electromagnetic radiation in the infrared, visible and ultra violet frequency region of the electromagnetic spectrum.

As used herein, the term "optical filter" is intended to mean a device for selectively passing or rejecting passage of radiation in a wavelength, polarization or frequency dependent manner. The term can include an interference filter in which multiple layers of dielectric materials pass or reflect radiation according to constructive or destructive interference between reflections from the various layers. Interference filters are also referred to in the art as dichroic filters, or dielectric filters. The term can include an absorptive filter which prevents passage of radiation having a selective wavelength or wavelength range by absorption. Absorptive filters include, for example, colored glass or liquid.

As used herein, the term "color optical filter" is used to describe an optical component having a surface on which a plurality of different "micro filters" (having different pass bands) is disposed. Suitable color optical filters include, for example, dielectric filters and pigmented transparent filters.

As used herein, the phrase "operatively coupled" refers to bringing two or more items together or into relationship with each other such that they may operate together or allow transfer of information between the two or more items.

As used herein, the terms "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, the phrase "polarizing filter" refers to a filter that filters incoming light to emit substantially only polarized light.

As used herein, the term "substantially," means at least 75 percent, preferably 90 percent, and most preferably at least 95 percent.

As used herein, the terms "surgeon" and "doctor" refers to any user of the head-mounted surgical illuminator as disclosed herein.

As used herein, the term "visible light" refers to light that is perceptible to the unaided human eye, generally in the wavelength range from about 400 to 700 nm.

As used herein, the term "ultraviolet radiation" refers to radiation whose wavelength is in the range from about 80 nm to about 400 nm.

As used herein, the terms "front," "back," "rear," "upper," "lower," "right," and "left" in this description are merely used to identify the various elements as they are oriented in the FIGS, with "front," "back," and "rear" being relative apparatus. These terms are not meant to limit the element which they describe, as the various elements may be oriented differently in various applications.

It will be understood that, although the terms first, second, etc. May be used herein to describe various elements, these elements should not be limited by these terms. These terms are only used to distinguish one element from another. For example, a first element could be termed a second element, and, similarly, a second element could be termed a first element without departing from the teachings of the disclosure.

The surgical illuminator 100 is shown in cross section in FIG. 1. A light emitting diode 110 is conventionally soldered to an aluminum printed circuit board 120. The light emitting diode 110 includes a light emitting diode die 111, generally contained within a light emitting diode body 112, having a spherical optical surface 113. The printed circuit board 120 is mounted in a base 121. The base 121 includes a feature 122 for fastening to a headlamp mounting bracket 123. The headlamp mounting bracket 123 is conventionally attached to a headband (not shown). Three helical grooves 124 are machined into base 121, evenly spaced 120 degrees apart. A slot in the base 121 contains an O-ring 152 for sealing against contaminants, as well as providing a controlled amount of friction for holding components in place.

The base 121 is deployed within a cylindrical lens barrel 130. The cylindrical lens barrel 130 includes three holes 131 through which three cam followers 132 are inserted, of which only one of the cam followers 132 is shown. The cam followers 132 protrude into helical grooves 124. A series of fins 133 are also machined into cylindrical lens barrel 130. The fins 133 increase the outside surface area of the cylindrical lens barrel 130 to improve its ability to dissipate heat. Further, the tips of fins 133 will naturally be cooler than the cylindrical lens barrel 130 and may be touched with a lower surface contact, making it easier for the user 135 to touch the assembly. A cylindrical knurled ring 134 is conventionally fastened to cylindrical lens barrel 130 using threads. The cylindrical knurled ring 134 has the effect of decreasing the surface area and thus thermal transfer to the operator when the operator adjusts the surgical illuminator 100.

Deployed within the cylindrical lens barrel 130 is an aspheric lens 140, having a planar surface 141 and a convex surface 142. The aspheric lens 140 may thus be described as "plano-aspheric." The aspheric lens 140 may be, for example, the Edmund Scientific Part Number 66013 (Scientifics Direct, Inc., Tonawanda, N.Y. 14150). In one embodiment, the aspheric lens 140 has a diameter of about 25 mm and a focal length of about 17.5 mm. The aspheric lens 140 includes a planar surface 141, deployed at object distance Do from light emitting diode die 111. The aspheric lens 140 further includes a convex aspheric lens convex surface 142. As is well understood in the field of optical system design, the aspheric lens convex surface 142 is not a constant radius, but best described by a complicated polynomial. Such surfaces are frequently used to correct for optical aberrations. Also deployed is a double convex lens 160, including inside 161 and outside 162 surfaces. The double convex lens 160 may be, for example, Edmund Scientifics Part Number 27745 (Scientifics Direct, Inc., Tonawanda, N.Y. 14150) and be of focal length of about 75 mm and diameter of about 25 mm. Both the aspheric lens 140 and the double convex lens 160 are preferably coated with an anti-reflective coating for optical efficiency.

A spacer 150, a square cross section O-ring 151, and retaining ring (not shown) hold the lenses 140 and 160 in place. A multi-conductor wire 125 from circuit board 120 passes through the back of the base 121 and connects to a switch 126 and a power source 127 to power the light emitting diode 110. The cylindrical lens barrel 130 includes threads 136 on the distal end, permitting the attachment of color filters and polarizing filters, both of which are not shown.

Figure 2:
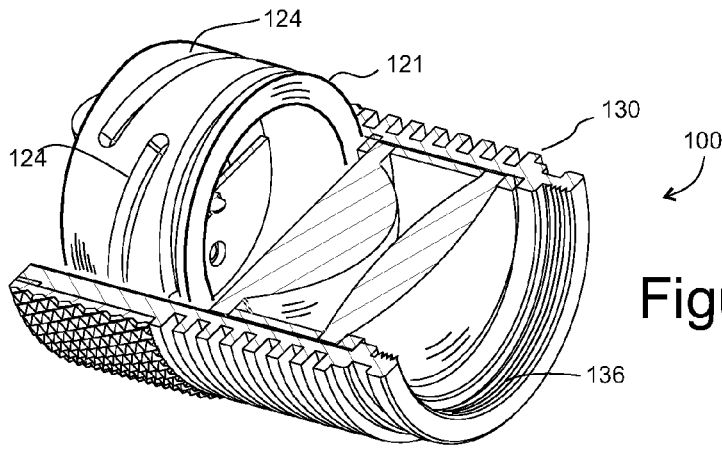
FIG. 2 is a perspective side-view cross-sectional drawing illustrating an exemplary surgical illuminator.

The details of the helical groove 124 are best understood by examining FIG. 2. FIG. 2 presents the surgical illuminator 100 in a cutaway view, wherein base 121 is present its entirety. Each of the three helical grooves 124 span about 270 degrees around the outer cylindrical surface of base 121. This large angular extent means that a large rotational movement of cylindrical lens barrel 130 is required for a small movement of the base within the barrel. Consequently, the surgical illuminator 100 is easy to adjust.

Figure 3:
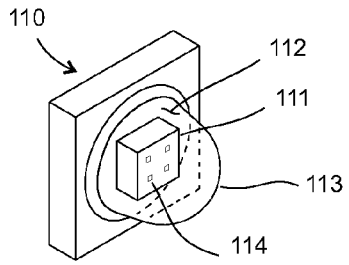
FIG. 3 is a perspective side-view drawing illustrating an exemplary light emitting diode.

FIG. 3 presents the details of light emitting diode 110. The light emitting diode die 111 takes the form of a glowing, extruded square. Some light emerges from the rectangular sides, but the light from the top is usefully directed toward the viewing plane. Metallization artifacts 114 are present on the top, square surface of the light emitting diode die 111, and these cast shadows. In one embodiment, the spherical surface 113 is about a 1 mm radius of curvature, and thus induces considerable focal power to the optical system, rendering a narrow output beam for light emitting diode 110. A suitable light emitting diode 110 for the surgical illuminator 100 may be, for example, part number LCW CQ7P manufactured by OSRAM Corporation (OSRAM GmbH, Munich, Germany). This light emitting diode 110 features a narrow, about 80 degree radiation pattern, and maximum forward current of about 800 mA.

The cylindrical lens barrel 130 can be made up of numerous components to perform the functions described herein; one need not utilize a generally tubular lens barrel as shown in the figures. Other configurations for the lens barrel 130 will be evident to those skilled in art based on their common general knowledge and the principles described herein. The cylindrical lens barrel 130 can be machined, particularly if it is made from metal. The cylindrical lens barrel 130 can be machined with a lathe such as a lathe or the like. Other materials for, and methods of manufacturing, the cylindrical lens barrel 130 will be evident to those skilled in art based on their common general knowledge and the principles described herein.

The aspheric lens 140 and/or the double convex lens 160 can be cast from a castable polymer such as acrylic, castable polycarbonate, or epoxy or the like. Both the aspheric lens 140 and the double convex lens 160 are mounted axially within the lens barrel 130. Alternatively, the aspheric lens 140 and/or the double convex lens 160 can be machined from a suitable material such as acrylic or thermoplastic polycarbonate and polished after machining. If the aspheric lens 140 and/or the double convex lens 160 are machined, they can be machined by means of a lathe such as a lathe or the like. Further alternatively, the aspheric lens 140 and/or the double convex lens 160 can be injection molded if shape distortions that occur during cooling can be avoided or fixed. The aspheric lens 140 and/or the double convex lens 160 can alternatively be made of a non-polymer material such as glass or quartz, or made of a polymer by means other than casting, machining, or injection molding. Other methods of manufacturing an aspheric lens 140 and/or the double convex lens 160 will be evident to those skilled in art based on their common general knowledge and the principles described herein.

Figure 4:
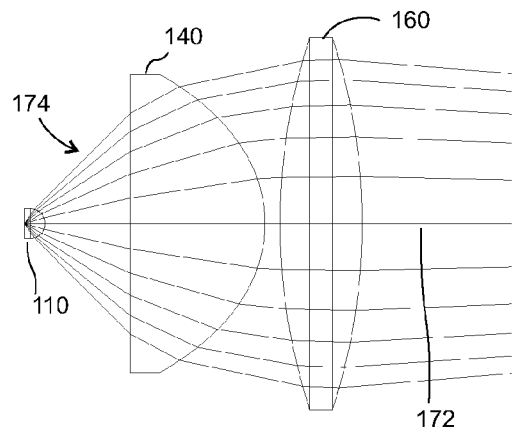
FIG. 4 is a side-view drawing illustrating an exemplary ray trace produced by an exemplary surgical illuminator.

The disposition of the optical elements of the surgical illuminator 100 is presented in FIG. 4, in the form of a ray trace. FIG. 4 shows how an evenly spaced fan of rays 174 makes its way from light emitting diode die 111, through light emitting diode spherical surface 113, the aspheric lens 140, and double-convex lens 160.

The surgical illuminator 100 has a multi-conductor cable 125 to receive electrical power for the light emitting diode 110 from an external power source 127. A power source, such as, for example, a lithium-ion AA or AAA batteries, could be provided internal to the surgical illuminator 100. Suitable current limiting means can be utilized to control, limit or regulate the magnitude of current flowing through the light emitting diode 110 to protect the light emitting diode 110 from excessive current that can otherwise flow. Such current limiting means would be preferably located at or within the external power source, where used, to minimize the size of the surgical illuminator 100. The external power source can be, for example, a battery pack with a switch and the current limiting means can be, for example, a resistor or a current regulator. Other means to receive power for the light emitting diode 110 will be evident to those skilled in art based on their common general knowledge and the principles described herein. As an example, the light emitting diode 110 could be directly connected to a battery power source within the surgical illuminator 100.

Figure 5:
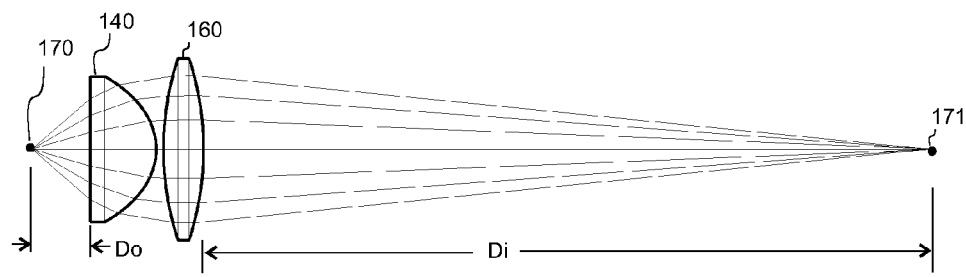
FIG. 5 is a side-view drawing illustrating an exemplary ray trace produced by an exemplary surgical illuminator.

FIG. 5 illustrates the optical details of how the lens is configured in one embodiment. The lens surfaces are designed so that an object at object focal point 170 that is about 8 mm from the planar surface 141 of the aspheric lens 140 focuses to an image design focal point 171 that is about 100 mm from outside surface of double-convex lens 160. The distance from double-convex lens 160 to image focal point 171 is referred to as Di. In FIG. 5, the object distance (Do) is about 8 mm and Di is about 100 mm. The optical system is symmetric about an optical axis 172. The positioning of the components is optimized using optical Computer-Aided Design (CAD) software such as Zemex, produced by Radiant Zemax (Radiant Zemax, Redmond, Wash., USA). The design configuration is not the operational configuration, as will be discussed herein below. In operation, the object distance (Do) is allowed to vary. Also, the image or viewing plane in operation is typically about 14 inches (35 cm), which is much greater than the image design focal point.

The details of the design optimization are typical for the surgical illuminator 100 to achieve its design objectives. Specifically, the designed focal point 170 presents a very narrow depth of focus. That is, even a small displacement of an object at object focal point 170 will cause the system to go out of focus. It will be later explained why this yields the round image spot. Next, planar surface 141 of aspheric lens 140 forms the optimal shape. A concave surface would gather more rays, and thus be brighter, but it would not permit the narrow depth of focus of the surgical illuminator 100. A convex surface would sacrifice brightness. Additionally, a convex surface would increase the system magnification, which would mean that it could only achieve a larger minimum spot size. The optical configuration of the surgical illuminator 100 makes the steepest deflections of the rays at the planar 141 and convex 142 surfaces the aspheric lens 140. This configuration allows aspheric lens convex surface 141 to properly correct for spherical aberration. The double convex lens 160 is left to do less of the work, because its aberrations are not corrected for. The double-convex lens 160 does, however, induce an additional 13 diopters of focal power into the optical system, contributing the narrow depth of focus.

During the operation of the surgical illuminator 100, referring to FIG. 3, the light emitting diode die 111 glows brightly causing the light rays 174 to be generated in all directions. A fan of such rays is presented, and they exit light emitting diode die 111 at surface 113. The rays 174 strike planar surface 141 of aspheric lens 140, and are deflected toward optical axis 172. Then, the rays 174 exit aspheric lens 140 at the convex surface 142, further bending toward optical axis 172. The inside surface of the double convex lens 161 and the outside surfaces of double convex lens 162 further deflect rays 174, and rays 174 emerge from the surgical illuminator 100 convergent.

The object distance (Do) may be adjusted by rotating cylindrical lens barrel 130, as may be seen in FIGS. 1 and 2. The cam followers 132 engage helical grooves 124, causing cylindrical lens barrel 130 to move longitudinally with respect to base 121. The surgeon makes such an adjustment to set the spot size of the surgical illuminator 100.

Figure 6A:
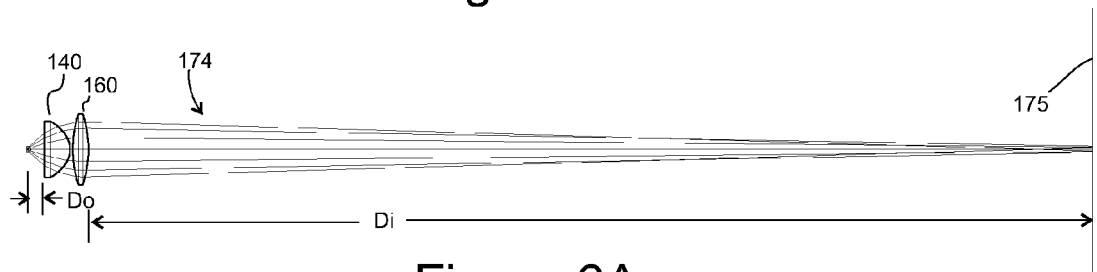
FIG. 6A is side-view drawing illustrating an exemplary ray trace produced by an exemplary surgical illuminator.

FIG. 6A show a ray trace of the surgical illuminator 100 adjusted for minimum spot size. So adjusted, Do is reduced to considerably less than the design focal point distance, so Do is about 4 mm. This causes the image focal point 171 to coincide with an image or viewing plane 175. In one embodiment, the viewing plane 175 is about 360 mm from double-convex lens 160 and the Di is about 360. In one embodiment, the light emitting diode die 111 is a square about 1 mm on each side and the illumination system provides magnification. So adjusted, the minimum spot size is about 1.5 inches (38 mm) in diameter, and with a peak brightness of about 125K lux. This is within the range of brightness produce by the fiber-optic illuminators that surgeons are familiar with.

The illumination spot formed on image plane is round and with sharp edges. The reason that the spot is round is that, when properly adjusted, object focal point 170 is positioned at the top of light emitting diode body 112. The top of light emitting diode body 112 presents a round, uniform surface 113 of the image onto the viewing plane 175. The light emitting diode die 111 is about 1 mm more distant from the aspheric lens 140. Because the depth of focus of the system is so narrow, the light emitting diode die 111 is effectively out of focus. This blurs together the light emitting diode die 111 surface anomalies such as metallization masks 114, wire bonds, or die imperfections. The resulting illumination is thus very high quality and uniform.

Figure 6B:
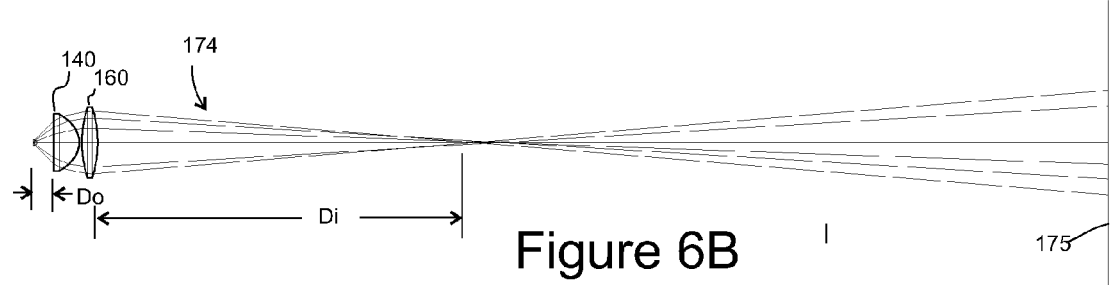
FIG. 6B is a side-view drawing illustrating an exemplary ray trace produced by an exemplary surgical illuminator.

FIG. 6B shows operation of the surgical illuminator 100 when it is adjusted for a large spot size. The base 121 is moved so that light emitting diode die 111 is about 8 mm from aspheric lens 140, or Do is about 8 mm. This movement is accomplished by rotating cylindrical lens barrel 130 (See, e.g., FIGS. 1 and 2). Because there are three evenly cam followers 132 with corresponding helical grooves 124, the movement is smooth and the forces evenly distributed. This brings image focal point 171 in to a distance of about 100 mm, so Di is about 100 mm. As seen in the FIG. 6B, rays 175 converge to image focal point 171, cross, and then diverge until they hit viewing plane 173. This operation is in contrast to conventional light emitting diode illuminators, which generally become more divergent when adjusted for larger spot size. The surgical illuminator 100 features a lower system magnification when adjusted for larger spot size. This at least partly compensates for the blurring effect from bringing the image focal point far from the viewing plane. By so doing, surgical illuminator 100 maintains reasonably sharp edges for the illumination spot, even when adjusted for maximum spot size.

Figure 7A:
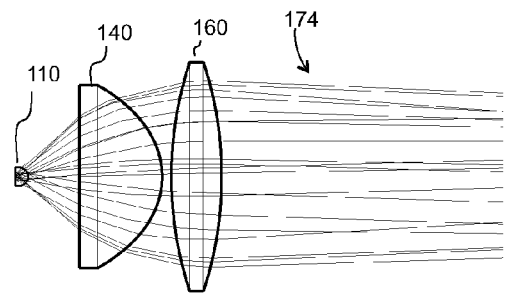
FIG. 7A is a side-view drawing illustrating an exemplary ray trace produced by an exemplary surgical illuminator.
Figure 7B:
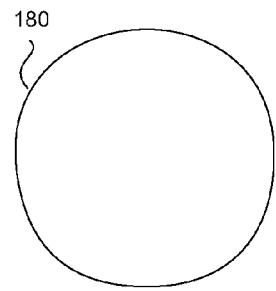
FIG. 7B is a top-view drawing illustrating an exemplary spot produced by an exemplary surgical illuminator.

FIGS. 7A and 7B further illustrate the performance of surgical illuminator 100. FIG. 7A shows a ray trace of randomly generated rays through the aspheric lens 140 and the double convex lens 160 of the surgical illuminator 100. FIG. 7A and the resulting analysis are generated with the aforementioned Zemax optical CAD software. FIG. 7A shows about 20 such rays, the software traces about one million for analysis purposes, and records the position and intensity with which they hit the viewing plane. The software is thus able to predict the performance of the surgical illuminator 100. The results of this analysis are presented in FIG. 7B. As can be seen from the FIG. 7B, an illumination spot 180 generated by the surgical illuminator 100 is a near perfect circle. This analysis comports with the performance of a physical implementation of the surgical illuminator 100.

The primary function of the operation of the surgical illuminator 100 is to get the rays to the proper places, and the secondary function is to conduct heat away from the die and into the ambient air. The aluminum printed circuit board 120 conducts heat to base 121, and some heat is additionally dissipated in the headlamp mounting bracket 123 to the headband. The base 121 conducts heat to cylindrical lens barrel 130. The knurling on the grip-ring 134, in addition to making it easy to grip, increases the surface area of the surgical illuminator 100, and thus its ability to dissipate heat. Further, the fins 133 additionally increase the surface area of the device.

Figure 8:
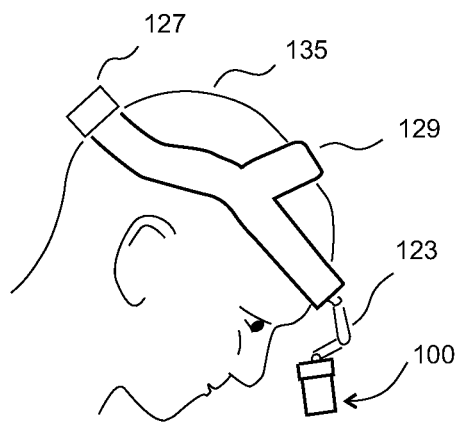
FIG. 8 is a side-view drawing illustrating an exemplary surgical illuminator worn by the user.

FIG. 8 is a side-view drawing illustrating the surgical illuminator 100 connected to the headlamp mounting bracket 123 mounted on the headband 129 and worn by the user 135.

Figure 9:
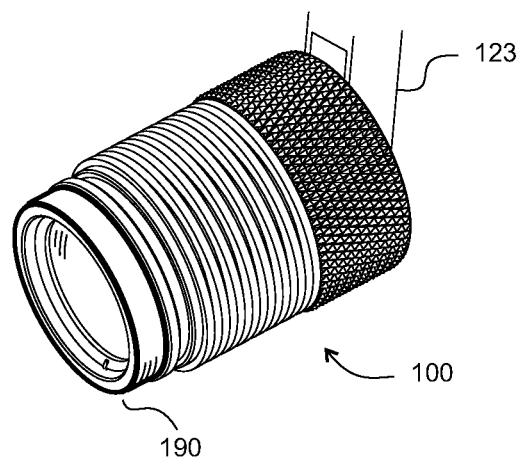
FIG. 9 is a perspective view drawing illustrating an exemplary surgical illuminator with a filter.

FIG. 9 is a perspective view drawing illustrating the headlamp mounting bracket 123 connected to the surgical illuminator 100. A filter 190 is connected to the front of the surgical illuminator 100. In one embodiment, the filter 190 is a camera lens. In one embodiment, the filter 190 is a camera lens of 25 mm. In one embodiment, the filter 190 is a circular polarizer lens. In one embodiment, the filter 190 is a magnification lens. In one embodiment, the filter 190 is a 10× magnification lens. Suitable circular polarizer lens and magnification lens may be obtained from, for example, Opteka (New York, N.Y.).

In one embodiment, the filter 190 is a color temperature filter that adjusts the current color temperature. Without the filter 190, the current color temperature is about 6100K. In one embodiment, the filter 190 is a color temperature filter of about 5500K. In one embodiment, the filter 190 is a color temperature filter of about 5000K. In one embodiment, the filter 190 is a color temperature filter of about 4500K. In one embodiment, the filter 190 is a color temperature filter of about 4000K. In one embodiment, the filter 190 is a color temperature filter of about 3500K.

Suitable color temperature filters may be obtained form, for example, Lee Filters (Andover, N.H.). Suitable color temperature filters are listed under the dichromic polycarbonate filters and may include, for example, filter part numbers 080, 206, 032, 205, and 042. For a discussion of how light can be used to enhance the visual image of tissues, please see, for example, U.S. Pat. No. 5,742,392.

Except as explicitly required by claim language, a single component may meet more than a single functional requirement, provided that the single substance or component fulfills the more than one functional requirement as specified by claim language.

All patents, patent applications, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Additionally, all claims in this application, and all priority applications, including but not limited to original claims, are hereby incorporated in their entirety into, and form a part of, the written description of the invention.

Applicants reserve the right to physically incorporate into this specification any and all materials and information from any such patents, applications, publications, scientific articles, web sites, electronically available information, and other referenced materials or documents. Applicants reserve the right to physically incorporate into any part of this document, including any part of the written description, the claims referred to above including but not limited to any original claims.

What is claimed is:

1. A surgical illuminator comprising:
a cylindrical lens barrel having a proximal end, a distal end, a first surface, and a second surface,
wherein the proximal end of the first surface of the cylindrical lens barrel comprises one or more holes,
a base having a first surface, second surface, and a third surface comprising one or more helical grooves,
wherein the base is mounted within the first surface of the cylindrical lens barrel with the one or more helical grooves and held in place with one or more cam followers protruding from the one or more holes into the one or more helical grooves,
wherein the one or more helical groves each independently span about 270 degrees;
a printed circuit board having a first surface and a second surface,
wherein the first surface of the printed circuit board is connected to the second surface of the base;
a light emitting diode coupled to the second surface of the printed circuit board;
an aspheric lens having a planar surface and a convex surface,
wherein the aspheric lens is mounted axially inside the cylindrical lens barrel so that the planar surface is facing the light emitting diode; and
a double-convex lens having a first surface and a second surface,
wherein the double-convex lens is mounted axially inside the cylindrical lens barrel so the convex surface of the aspheric lens is facing the first surface of the double-convex lens.

2. The surgical illuminator of claim 1, wherein the first surface of the base is connected to a headlamp mounting bracket on a headlamp band.

3. The surgical illuminator of claim 1, wherein the light emitting diode comprises a light emitting die contained within a light emitting diode body having a spherical optical surface having about a 1 mm radius of curvature.

4. The surgical illuminator of claim 3, wherein an exterior surface of the light emitting die comprises one or more surface metallization artifacts.

5. The surgical illuminator of claim 1, wherein the light emitting diode features about an 80 degree radiation pattern, and maximum forward current of about 800 mA.

6. The surgical illuminator of claim 1, wherein the light emitting diode operates with a current of about 100 mA to about 800 mA.

7. The surgical illuminator of claim 1, further comprising a power source operatively connected to the printed circuit board and an on/off switch.

8. The surgical illuminator of claim 1, wherein a distance (Do) between the second surface of the printed circuit board and the planar surface of the aspheric lens is from about 8 mm.

9. The surgical illuminator of claim 1, wherein the aspheric lens has a diameter of about 25 mm and a focal length of about 17.5 mm.

10. The surgical illuminator of claim 1, wherein the double convex lens has a diameter of about 25 mm and a focal length of about 75 mm.

11. The surgical illuminator of claim 1, further comprising a spacer between the convex surface of the aspheric lens and the first surface of the double-convex lens.

12. The surgical illuminator of claim 1, further comprising one or more filters detachably and axially mounted to the distal end of the cylindrical lens barrel.

13. The surgical illuminator of claim 1, further comprising a slot in third surface of the base containing an O-ring.

14. The surgical illuminator of claim 1, wherein the proximal end of the second surface of the cylindrical lens barrel is connected to a cylindrical knurled ring with threads.

15. The surgical illuminator of claim 1, wherein the distal end of the second surface of the cylindrical lens barrel comprises one or more fins.

16. A surgical illuminator comprising:
a cylindrical lens barrel having a proximal end, a distal end, a first surface, and a second surface,
wherein the proximal end of the second surface of the cylindrical lens barrel is connected to a cylindrical knurled ring with threads,
wherein the proximal end of the first surface of the cylindrical lens barrel comprises one or more holes,
wherein the distal end of the second surface of the cylindrical lens barrel comprises one or more fins;
a base having a first surface, second surface, and a third surface comprising one or more helical grooves,
wherein the base is mounted within the first surface of the cylindrical lens barrel with the one or more helical grooves and held in place with one or more cam followers protruding from the one or more holes into the one or more helical grooves,
wherein the first surface of the base is connected to a headlamp mounting bracket, wherein the one or more helical groves each independently span about 270 degrees;
a printed circuit board having a first surface and a second surface,
  wherein the first surface of the printed circuit board is connected to the second surface of the base;
a light emitting diode coupled to the second surface of the printed circuit board,
  wherein the light emitting diode comprises a light emitting die contained within a light emitting diode body having a spherical optical surface having about a 1 mm radius of curvature,
  wherein an exterior surface of the light emitting die comprises one or more surface metallization artifacts,
an aspheric lens having a planar surface and a convex surface,
  wherein the aspheric lens is mounted axially inside the cylindrical lens barrel so that the planar surface is facing the light emitting diode,
  wherein a distance (Do) between the second surface of the printed circuit board and the planar surface of the aspheric lens is from about 8 mm,
  wherein the aspheric lens has a diameter of about 25 mm and a focal length of about 17.5 mm; and
a double-convex lens having a first surface and a second surface,
  wherein the double-convex lens is mounted axially inside the cylindrical lens barrel so the convex surface of the aspheric lens is facing the first surface of the double-convex lens,
  wherein the double convex lens has a diameter of about 25 mm and a focal length of about 75 mm,
  wherein a distance between the convex surface of the aspheric lens and the first surface of the double-convex lens is set with a spacer.

17. The surgical illuminator of claim 16, wherein the light emitting diode features about an 80 degree radiation pattern, and maximum forward current of about 800 mA.

18. The surgical illuminator of claim 16, wherein the light emitting diode operates with a current of about 100 mA to about 800 mA.

19. The surgical illuminator of claim 16, further comprising a power source operatively connected to the printed circuit board and an on/off switch.

20. The surgical illuminator of claim 16, further comprising one or more filters detachably and axially mounted to the distal end of the cylindrical lens barrel.

21. The surgical illuminator of claim 16, further comprising a headlamp band connected to the headlamp mounting bracket.

22. A surgical illuminator comprising:
a cylindrical lens barrel having a proximal end, a distal end, a first surface, and a second surface,
  wherein the proximal end of the second surface of the cylindrical lens barrel is connected to a cylindrical knurled ring with threads,
  wherein the proximal end of the first surface of the cylindrical lens barrel comprises one or more holes,
  wherein the distal end of the second surface of the cylindrical lens barrel comprises one or more fins;
a base having a first surface, second surface, and a third surface comprising one or more helical grooves,
  wherein the base is mounted within the first surface of the cylindrical lens barrel with the one or more helical grooves and held in place with one or more cam followers protruding from the one or more holes into the one or more helical grooves,
  wherein the first surface of the base is connected to a headlamp mounting bracket,
  wherein the one or more helical groves each independently span about 270 degrees;
a printed circuit board having a first surface and a second surface,
  wherein the first surface of the printed circuit board is connected to the second surface of the base;
a light emitting diode coupled to the second surface of the printed circuit board,
  wherein the light emitting diode comprises a light emitting die contained within a light emitting diode body having a spherical optical surface having about a 1 mm radius of curvature,
  wherein an exterior surface of the light emitting die comprises one or more surface metallization artifacts,
  wherein the light emitting diode features about an 80 degree radiation pattern, and maximum forward current of about 800 mA,
  wherein the light emitting diode operates with a current of about 100 mA to about 800 mA;
a power source operatively connected to the printed circuit board,
  wherein the power source comprises an on/off switch;
an aspheric lens having a planar surface and a convex surface,
  wherein the aspheric lens is mounted axially inside the cylindrical lens barrel so that the planar surface is facing the light emitting diode,
  wherein a distance (Do) between the second surface of the printed circuit board and the planar surface of the aspheric lens is from about 8 mm,
  wherein the aspheric lens has a diameter of about 25 mm and a focal length of about 17.5 mm;
a double-convex lens having a first surface and a second surface,
  wherein the double-convex lens is mounted axially inside the cylindrical lens barrel so the convex surface of the aspheric lens is facing the first surface of the double-convex lens,
  wherein the double convex lens has a diameter of about 25 mm and a focal length of about 75 mm,
  wherein a distance between the convex surface of the aspheric lens and the first surface of the double-convex lens is set with a spacer;
one or more filters detachably and axially mounted to the distal end of the cylindrical lens barrel; and
a headlamp band connected to the headlamp mounting bracket.

23. A surgical illuminator comprising:
a cylindrical lens barrel having a proximal end, a distal end, a first surface, and a second surface,
  wherein the proximal end of the first surface of the cylindrical lens barrel comprises one or more holes,
a base having a first surface, second surface, and a third surface comprising one or more helical grooves,
  wherein the base is mounted within the first surface of the cylindrical lens barrel with the one or more helical grooves and held in place with one or more cam followers protruding from the one or more holes into the one or more helical grooves,
  wherein the one or more helical groves each independently span about 270 degrees;
a printed circuit board having a first surface and a second surface,
  wherein the first surface of the printed circuit board is connected to the second surface of the base;

a light emitting diode coupled to the second surface of the printed circuit board, wherein the light emitting diode includes a light emitting diode die;

an aspheric lens having a planar surface and a convex surface,
   wherein the aspheric lens is mounted axially inside the cylindrical lens barrel so that the planar surface is facing the light emitting diode; and a double-convex lens having a first surface and a second surface,
   wherein the double-convex lens is mounted axially inside the cylindrical lens barrel so the convex surface of the aspheric lens is facing the first surface of the double-convex lens;

wherein the aspheric lens and the double convex lens gather one or more light rays from an object focal point located on the light emitting diode die and focusing the one or more light rays onto an image focal point an image focusing distance away from the double-convex lens; and wherein rotation of the cylindrical barrel about the base permits the image focusing point to be adjusted over a range comprising at least 100 mm to 300 mm, and thereby producing an adjustable illumination spot size on an image plane.

24. The surgical illuminator of claim 23, wherein the gathering of the one or more light rays from an object focal point located on the light emitting die is further characterized as having a narrow depth of focus.

* * * * *